United States Patent [19]
Baird et al.

[11] 4,313,765
[45] Feb. 2, 1982

[54] SYNERGISTIC BLENDS OF CELLULASE-FREE XANTHAN GUM AND CELLULOSICS

[75] Inventors: John K. Baird, San Diego; Paul A. Sandford, Del Mar; Jaewon L. Shim, San Diego, all of Calif.

[73] Assignee: Merck & Co., Inc., Rahway, N.J.

[21] Appl. No.: 190,546

[22] Filed: Sep. 24, 1980

[51] Int. Cl.$^3$ .......................... C09L 1/28; C09L 5/00
[52] U.S. Cl. ............................. 106/197 C; 106/197 R; 106/316
[58] Field of Search ............... 106/197 R, 197 C, 316; 536/114

[56] References Cited

U.S. PATENT DOCUMENTS

| | | | |
|---|---|---|---|
| 3,658,734 | 4/1972 | Pettitt . | |
| 3,765,918 | 10/1973 | Jordan et al. | 106/205 |
| 4,067,389 | 7/1976 | Savins | 166/246 |
| 4,070,535 | 1/1978 | Empey et al. | 536/114 |
| 4,169,818 | 10/1979 | DeMartino . | |

OTHER PUBLICATIONS

Ott et al., "Cellulose", High Polymers, vol. V, Part II, pp. 938 & 945.

*Primary Examiner*—Allan Lieberman
*Attorney, Agent, or Firm*—Gabriel Lopez; Hesna J. Pfeiffer

[57] ABSTRACT

This invention relates to a blend of cellulase-free xanthan gum with a number of cellulosics, including carboxymethyl cellulose, hydroxyethyl cellulose and hydroxypropylmethyl cellulose. At 1:1 weight ratio, these blends show surprising viscosities when tested in aqueous solutions of 1%, 0.5%, 0.25% and 0.1% total gum concentration. The blends have utility in any application where cellulosics are used as thickeners, such as industrial or food applications, e.g., toothpaste, or drink mix formulations.

4 Claims, No Drawings

SYNERGISTIC BLENDS OF CELLULASE-FREE XANTHAN GUM AND CELLULOSICS

RELATIONSHIP TO THE PRIOR ART

Different gum blends are widely known and used. It has been found that the described blends show unusual synergism and are not suggested by the prior art. Generally cellulosics were incompatible with xanthan gum, due to presence in the latter of various cellulase enzymes. However, cellulosics, although widely used, suffer, to varying degrees in different applications from salt incompatibility, instability to heat, limited shelf life, instability to pH changes, and unpleasant or undesirable mouth-feel in certain compositions such as toothpaste.

However, if cellulosics were mixed with many other gums in order to improve these characteristics, the final viscosity was usually detrimentally affected.

It has now been found that cellulosics, including carboxymethylcellulose, hydroxyethylcellulose, or hydroxypropylmethylcellulose, can be mixed with cellulase-free xanthan gum. Not only are the desirable properties of the cellulosics retained and the undesirable properties of cellulosics minimized, but the resulting viscosities of the solutions prepared from these blends is surprisingly and unexpectedly higher than that predicted from measurements of either component alone.

The synergistic effect can be demonstrated in synthetic tap water (STW) on 1:1 (weight basis) blends, thereby keeping the good qualities of cellulosics with a 50% dilution, and the good qualities of xanthan gum at 50% dilution, while maintaining and even increasing viscosity of solutions of these 1:1 blends. The synergistic effect in viscosity can be demonstrated at 1%, 0.5%, 0.25% and 0.1% concentration levels in Synthetic Tap Water (STW); the synergism is not as pronounced in deionized water.

THE MATERIALS USED

The cellulosics useful in this invention are all the commercially available forms of cellulosics, including carboxymethylcellulose, hydroxyethylcellulose, hydroxypropylmethylcellulose, or microcrystalline cellulose. Other commonly known or used cellulosics can be also employed.

The cellulase-free xanthan gum can be any of a number of grades available. One form is produced by treating xanthan gum beer with alkali metal hypochlorite, pH 6 to 7, at concentration levels of 0.08–0.1% by weight and about 30° C. for 6–8 hours, followed by heating to 85°–95° C. for several minutes, then recovering, by precipitating the cellulase-free beer, and by drying and milling the presscake. Other methods include treatment of xanthan gum beer with mercury compounds, treatment of xanthan gum beer presscakes with propylene oxide, and heating xanthan gum beer that has been adjusted to high pH to about 90° C. followed by cooling and neutralization.

FORMING THE BLEND

The two gums are dry blended, at about a 1:1 weight ratio, by rolling or any other such technique. Another method involves adding the desired cellulosic to cellulase-free xanthan gum beer, and then recovering the blend using the normal recovery steps for xanthan gum alone.

USING THE BLEND

These blends can be employed in any formulation where cellulosics are used, such as toothpastes or drink mixes. A formulation for toothpaste using this blend follows:

| TOOTHPASTE | % | gm |
|---|---|---|
| Sorbitol | 12.5 | 500 |
| Glycerol | 12.5 | 500 |
| DCPD (dicalcium phosphate dihydrate) | 45.0 | 1800 |
| Sodium lauryl sulfate | 1.5 | 60 |
| Methylparaben | 0.15 | 6 |
| Titanium dioxide | 0.75 | 30 |
| Saccharin | 0.15 | 6 |
| Flavor | 1.0 | 40 |
| Color | 0.02 | 0.8 |
| Water | 25.43 | 1017.2 |
| Carboxymethylcellulose | 0.5 | 40 |
| Xanthan gum, cellulase free | 0.5 | 40 |
| | 100.0% | 4000 g. |

The final toothpaste was completely suitable.

DETERMINATION OF SYNERGISM

Data was determined for 1%, 0.5%, 0.25%, and 0.1% concentration of a 1:1 blend of the indicated gums. Two methods were used to calculate theoretical expected values, one the log-plot (see U.S. Pat. No. 4,169,818 for reference to this method) the other, the sum of ½ viscosities. Values were also calculated by mathematical average, but these were not considered as reliable and are not included. The data is summarized in Tables I, II, III and IV.

TABLE I

% Synergism of Cellulase-Free XG with Cellulosics in STW[1]: 1.0% Total Solids

| | Gum Viscosity | | Blend Viscosity (1:1) | | |
|---|---|---|---|---|---|
| Sample | 0.5% Viscosity/STW | 1.0% Viscosity/STW | Viscosity A Experimental | Viscosity B Theoretical Value[2] | % Synergism[3] |
| Carboxymethylcellulose, 7HOF | 92.5 | 626 | 1150 | (a) 995<br>(b) 622.5 | + 16<br>+ 85 |
| Hydroxyethylcellulose, QP4400 | 57.5 | 550 | 1220 | (a) 935<br>(b) 587.5 | + 30<br>+108 |
| Hydroxypropylmethyl cellulose, Methocel, 90HG | 20.5 | 115 | 1000 | (a) 500<br>(b) 550.5 | +100<br>+ 82 |
| Cellulase-free xanthan gum (Produced by hypochlorite treat- | 530 | 1586 | — | — | — |

TABLE I-continued

% Synergism of Cellulase-Free XG with Cellulosics in STW[1]: 1.0% Total Solids

| | Gum Viscosity | | Blend Viscosity (1:1) | | |
|---|---|---|---|---|---|
| Sample | 0.5% Viscosity/STW | 1.0% Viscosity/STW | Viscosity A Experimental | Viscosity B Theoretical Value[2] | % Synergism[3] |
| ment) | | | | | |

[1]synthetic tap water - 1000 ppm NaCl & 143 ppm $CaCl_2 \cdot 2H_2O$ in D.I. water.
[2](a) calculated from log-plot of 1.0% viscosities.
(b) calculated from sum of 0.5% viscosities.
[3]% synergism = $\frac{\text{Viscosity A} - \text{Viscosity B}}{\text{Viscosity B}} \times 100$

TABLE II

% Synergism of Cellulase-Free XG with Cellulosics in STW[1]: 0.5% Total Solids

| | Gum Viscosity | | Blend Viscosity (1:1) | | |
|---|---|---|---|---|---|
| Sample | 0.25% Viscosity/STW | 0.5% Viscosity/STW | Viscosity A Experimental | Viscosity B Theoretical Value[2] | % Synergism[3] |
| Carboxymethylcellulose, 7HOF | 19.5 | 84.5 | 247.5 | (a) 198<br>(b) 154.5 | + 25<br>+ 60 |
| Hydroxyethylcellulose, QP4400 | 10 | 40 | 230 | (a) 136<br>(b) 142 | + 69<br>+ 59 |
| Hydroxypropylmethyl cellulose Methocel, 90HG | 7 | 20.5 | 200 | (a) 98<br>(b) 142 | +104<br>+ 41 |
| Cellulase-free xanthan gum (produced by hypochlorite treatment) | 135 | 466.3 | — | — | — |

[1]Synthetic tap water - 1000 ppm NaCl and 143 ppm $CaCl_2 \cdot 2H_2O$ in D.I. water.
[2](a) calculated from log-plot of 0.5% viscosities
(b) calculated from sum of 0.25% viscosities.
[3]% synergism = $\frac{\text{Viscosity A} - \text{Viscosity B}}{\text{Viscosity B}} \times 100$

TABLE III

% Synergism of Cellulase-Free XG with Cellulosics in STW[1]: 0.25% Total Solids

| | Gum Viscosity | | Blend Viscosity (1:1) | | |
|---|---|---|---|---|---|
| Sample | 0.125% Viscosity/STW | 0.25% Viscosity/STW | Viscosity A Experimental | Viscosity B Theoretical Value[2] | % Synergism[3] |
| Carboxymethylcellulose, 7HOF | 7.8 | 19.5 | 56.5 | (a) 52<br>(b) 48.4 | + 9<br>+17 |
| Hydroxyethylcellulose, QP4400 | 3.25 | 10 | 50 | (a) 37<br>(b) 43.85 | +35<br>+14 |
| Hydroxypropylmethyl cellulose, Methocel 90HG | 3.8 | 7 | 44.5 | (a) 31<br>(b) 44.4 | +44<br>+0.2 |
| Cellulase-free xanthan gum (Produced by hypochlorite treatment) | 40.6 | 135 | — | — | — |

[1]Synthetic tap water - 1000 ppm NaCl and 143 ppm $CaCl_2 \cdot 2H_2O$ in D.I. water.
[2](a) calculated from log-plot of 0.25% viscosities.
(b) calculated from sum of 0.125% viscosities.
[3]% synergism = $\frac{\text{Viscosity A} - \text{Viscosity B}}{\text{Viscosity B}} \times 100$

TABLE IV

% Synergism of Cellulase-Free XG with Cellulosics in STW[1]: 0.1% Total Solids

| | Gum Viscosity | | Blend Viscosity (1:1) | | |
|---|---|---|---|---|---|
| Sample | 0.05% Viscosity/STW | 0.1% Viscosity/STW | Viscosity A Experimental | Viscosity B Theoretical Value[2] | % Synergism[3] |
| Carboxymethylcellulose, 7HOF | 3.5 | 6.5 | 15.0 | (a) 14.3<br>(b) 12.5 | + 5<br>+20 |
| Hydroxy- | 2.5 | 3.9 | 12.5 | (a) 11.0 | +14 |

TABLE IV-continued

% Synergism of Cellulase-Free XG with Cellulosics in STW[1]: 0.1% Total Solids

| Sample | Gum Viscosity 0.05% Viscosity/STW | Gum Viscosity 0.1% Viscosity/STW | Blend Viscosity (1:1) Viscosity A Experimental | Blend Viscosity (1:1) Viscosity B Theoretical Value[2] | % Synergism[3] |
|---|---|---|---|---|---|
| ethylcellulose, QP4400 | | | | (b) 11.5 | +9 |
| Hydroxypropylmethyl cellulose, Methocel, 90HG | 4.0 | 6.0 | 16.0 | (a) 13.6<br>(b) 13.0 | +18<br>+23 |
| Cellulase-free xanthan gum (Produced by hypochlorite treatment) | 9.0 | 31.5 | — | — | — |

[1] Synthetic tap water - 1000 ppm NaCl and 143 ppm CaCl$_2$ . 2H$_2$O in D.I. water.
[2] (a) Calculated from log-plot of 0.1% viscosities.
(b) Calculated from sum of 0.05% viscosities.
[3] % Synergism = $\frac{\text{Viscosity A} - \text{Viscosity B}}{\text{Viscosity B}} \times 100$ Other data were obtained by dissolving the dry gum powder blends (1:1) in 1% KCl and viscosities (1% total solids) measured using a Brookfield LVF viscometer, spindle No. 3 at 60 rpm, and are shown in Table V.

TABLE V

% Synergism of Cellulase-Free XG with Cellulosics in 1% KCl: 1% Total Solids

| Sample | Gum Viscosity 1% Viscosity/KCl | Blend Viscosity (1:1) Viscosity A Experimental | Blend Viscosity (1:1) Viscosity B Theoretical Value[1] | % Synergism[2] |
|---|---|---|---|---|
| Carboxymethylcellulose, 7HOF | 860 | 1180 | 1150 | 3 |
| Hydroxyethylcellulose | 310 | 820 | 680 | 21 |
| Hydroxypropylmethylcellulose Methocel 90HG | 180 | 780 | 520 | 50 |
| Cellulase-free xanthan gum | 1500 | — | — | — |

[1] Calculated from log plots of 1.0% viscosities.
[2] % Synergism = $\frac{\text{Viscosity A} - \text{Viscosity B}}{\text{Viscosity B}} \times 100$

What is claimed is:

1. A 1:1 (weight basis) blend composition of cellulase-free xanthan gum and either carboxymethylcellulose, hydroxyethylcellulose or hydroxypropylmethylcellulose.

2. The composition of claim 1 in which carboxymethylcellulose is used.

3. The composition of claim 1 in which hydroxyethylcellulose is used.

4. The composition of claim 1 in which hydroxypropylmethylcellulose is used.

* * * * *